United States Patent
Lee

(10) Patent No.: US 10,345,226 B1
(45) Date of Patent: Jul. 9, 2019

(54) SPECTRUM ADJUSTER AND PRODUCING A PURE ANALYTE SPECTRUM

(71) Applicant: The United States of America, as represented by the Secretary of Commerce, Washington, DC (US)

(72) Inventor: Young Jong Lee, Gaithersburg, MD (US)

(73) Assignee: THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 0 days.

(21) Appl. No.: 16/164,859

(22) Filed: Oct. 19, 2018

Related U.S. Application Data

(60) Provisional application No. 62/619,253, filed on Jan. 19, 2018.

(51) Int. Cl.
*G01N 21/25* (2006.01)
*G01N 21/31* (2006.01)

(52) U.S. Cl.
CPC ........... *G01N 21/255* (2013.01); *G01N 21/31* (2013.01); *G01N 2201/0691* (2013.01)

(58) Field of Classification Search
CPC ........ G01N 21/00; G01N 21/03; G01N 21/05; G01N 21/31; G01N 21/39; G01N 21/61; G01N 21/62; G01N 21/65; G01N 21/255; G01N 21/274; G01N 21/3577; G01N 2201/0691; G01N 23/06; G01J 3/28; G01J 3/42; G01J 3/44; G01J 3/427; A61B 5/14532; A61B 5/1455; C12Q 1/02; C12M 1/34; H05B 41/28; H05B 33/08; H05B 37/02; G01B 9/02; G01B 11/02
See application file for complete search history.

(56) References Cited

U.S. PATENT DOCUMENTS

| | | | | |
|---|---|---|---|---|
| 5,206,711 A | * | 4/1993 | Berthold | G01N 21/8507 356/435 |
| 2011/0070602 A1 | * | 3/2011 | Thomson | G01N 21/552 435/29 |

* cited by examiner

*Primary Examiner* — Jamil Ahmed
(74) *Attorney, Agent, or Firm* — Office of Chief Counsel for National Institute of Standards and Technology

(57) ABSTRACT

A spectrum adjuster produces a pure analyte spectrum and includes: a dynamic opacity optic that receives input light, receives an adjustment signal, produces primary adjusted light, and produces secondary adjusted light from the input light based on the adjustment signal; a light source in optical communication with the dynamic opacity optic; a detector in optical communication with the dynamic opacity optic and that receives transmitted light from the sample and produces a transmitted light signal based on an amount of transmitted light received; and an adjustment controller that receives the transmitted light signal, produces the adjustment signal, and communicates the adjustment signal to the dynamic opacity optic.

10 Claims, 9 Drawing Sheets

SPECTRUM ADJUSTER AND PRODUCING A PURE ANALYTE SPECTRUM

CROSS REFERENCE TO RELATED APPLICATIONS

The application claims priority to U.S. Provisional Patent Application Ser. No. 62/619,253 filed Jan. 19, 2018, the disclosure of which is incorporated herein by reference in its entirety.

STATEMENT REGARDING FEDERALLY SPONSORED RESEARCH

This invention was made with United States Government support from the National Institute of Standards and Technology (NIST), an agency of the United States Department of Commerce. The Government has certain rights in the invention. Licensing inquiries may be directed to the Technology Partnerships Office, NIST, Gaithersburg, Md., 20899; voice (301) 301-975-2573; email tpo@nist.gov; reference NIST Docket Number 18-007US1.

BRIEF DESCRIPTION

Disclosed is a spectrum adjuster to produce a pure analyte spectrum of a sample, the spectrum adjuster comprising: a dynamic opacity optic that: receives input light; receives an adjustment signal; produces primary adjusted light from the input light based on the adjustment signal such that an intensity of the primary adjusted light is based on an amount of primary transmitted light transmitted through the sample in an absence of an analyte; and produces secondary adjusted light from the input light based on the adjustment signal such that an intensity of the secondary adjusted light is based on an amount of secondary transmitted light transmitted through the sample in a presence the analyte; a light source in optical communication with the dynamic opacity optic and that communicates the input light to the dynamic opacity optic; a detector in optical communication with the dynamic opacity optic and that: receives transmitted light from the sample; and produces a transmitted light signal based on an amount of transmitted light received from the sample; and an adjustment controller in communication with the detector and the dynamic opacity optic and that: receives the transmitted light signal from the detector; produces the adjustment signal based on the transmitted light signal; and communicates the adjustment signal to the dynamic opacity optic, the dynamic opacity optic being optically interposed between the light source and the detector, and the sample when present being optically interposed between the dynamic opacity optic and the detector.

Disclosed is a process for producing a secondary adjusted light, the process comprising: producing an input light; receiving, by a dynamic opacity optic, the input light; producing, by the dynamic opacity optic, a primary adjusted light from the input light; subjecting a sample in an absence of an analyte to the primary adjusted light; communicating, from the sample, primary transmitted light, in response to subjecting the sample in the absence of the analyte to the primary adjusted light; receiving, by a detector, the primary transmitted light; producing, by the detector, a transmitted light signal based on the primary transmitted light; receiving, by an adjustment controller, the transmitted light signal from the detector; producing, by the adjustment controller, an adjustment signal based on the transmitted light signal; communicating the adjustment signal from the adjustment controller to the dynamic opacity optic; and producing, by the dynamic opacity optic, a secondary adjusted light based on the adjustment signal to produce the secondary adjusted light.

Disclosed is a process for producing a pure analyte spectrum, the process comprising: producing an input light; receiving, by a dynamic opacity optic, the input light; producing, by the dynamic opacity optic, a primary adjusted light from the input light; subjecting a sample in an absence of an analyte to the primary adjusted light; communicating, from the sample, primary transmitted light, in response to subjecting the sample in the absence of the analyte to the primary adjusted light; receiving, by a detector, the primary transmitted light; producing, by the detector, a transmitted light signal based on the primary transmitted light; receiving, by an adjustment controller, the transmitted light signal from the detector; producing, by the adjustment controller, an adjustment signal based on the transmitted light signal; communicating the adjustment signal from the adjustment controller to the dynamic opacity optic; and producing, by the dynamic opacity optic, a secondary adjusted light based on the adjustment signal; subjecting the sample comprising the analyte to the secondary adjusted light; communicating, from the sample, secondary transmitted light in response to subjecting the sample in presence of the analyte to the primary adjusted light; receiving, by the detector, the secondary transmitted light; producing, by the detector, the transmitted light signal based on the secondary transmitted light; receiving, by a spectrum analyzer, the transmitted light signal from the detector; and converting the transmitted light signal into the pure analyte spectrum to produce the pure analyte spectrum.

BRIEF DESCRIPTION OF THE DRAWINGS

The following description should not be considered limiting in any way. With reference to the accompanying drawings, like elements are numbered alike.

DETAILED DESCRIPTION

A detailed description of one or more embodiments is presented herein by way of exemplification and not limitation.

It has been discovered that a spectrum adjuster adjusts incident light intensity as a function of wavelength to reference-only transmitted light such that output adjusted light has uniform intensity over a selected spectral range. Advantageously, when a strong absorption band of a matrix such as a reference or solvent is present in a selected spectral region, e.g., of a solute such as a strong water absorption near an amide absorption band of a protein, the spectrum adjuster overcomes difficulties and shortcomings of a conventional spectrometer that has limited detection capability of a relatively dilute analyte contribution to a large signal from a strong solvent absorption band when the conventional spectrometer has limited dynamic range of its detection system. Beneficially, the spectrum adjuster decreases a contribution to a transmission signal of a matrix and increases a contribution of absorption of the analyte to the transmission spectrum that is within a dynamic range of a photodetector.

Figure 1:
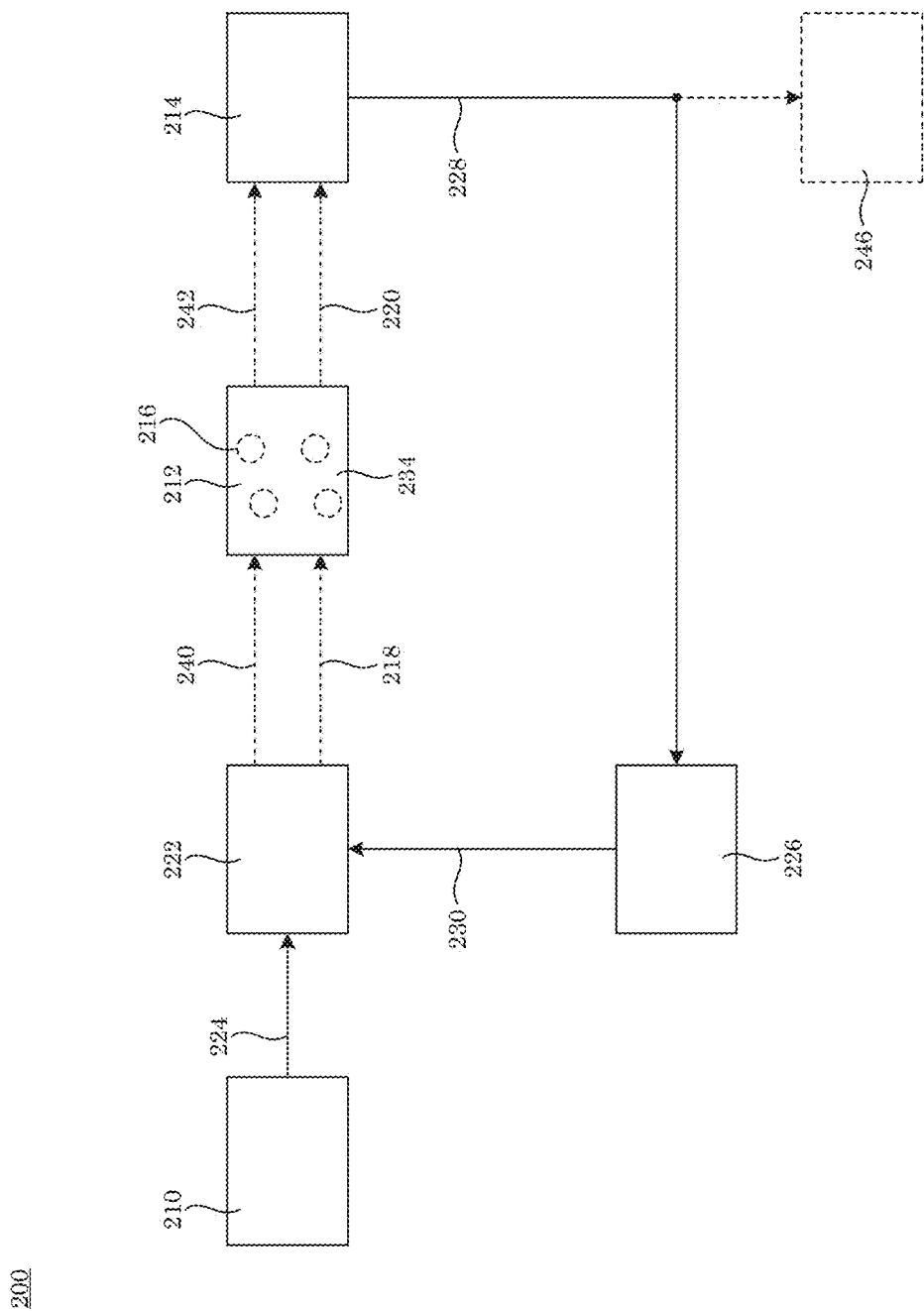
FIG. 1 shows a spectrum adjuster with a sample interposed between a dynamic opacity optic and a detector.

Spectrum adjuster 200 produces pure analyte spectrum 232 of analyte 216 disposed in sample 212. In an embodiment, with reference to FIG. 1, spectrum adjuster 200 includes dynamic opacity optic 222. Dynamic opacity optic 222 receives input light 224, receives adjustment signal 230, and produces primary adjusted light 240 from input light 224 based on adjustment signal 230. An intensity of primary adjusted light 240 is based on an amount of primary transmitted light 242 transmitted through sample 212 in an absence of analyte 216. Further, dynamic opacity optic 222 produces secondary adjusted light 218 from input light 224 based on adjustment signal 230 such that an intensity of secondary adjusted light 218 is based on an amount of secondary transmitted light 220 transmitted through sample 212 in a presence analyte 216. Spectrum adjuster 200 also includes light source 210 in optical communication with dynamic opacity optic 222 that communicates input light 224 to dynamic opacity optic 222. Detector 214 is in optical communication with dynamic opacity optic 222 and receives secondary transmitted light 220 from sample 212 and produces transmitted light signal 228 based on an amount of secondary transmitted light 220 received from sample 212. Adjustment controller 226 is in communication with detector 214 and dynamic opacity optic 222. Here, adjustment controller 226 receives transmitted light signal 228 from detector 214, produces adjustment signal 230 based on transmitted light signal 228, and communicates adjustment signal 230 to dynamic opacity optic 222. Dynamic opacity optic 222 is optically interposed between light source 210 and detector 214. Sample 212, when present, is optically interposed between dynamic opacity optic 222 and detector 214.

Figure 2:
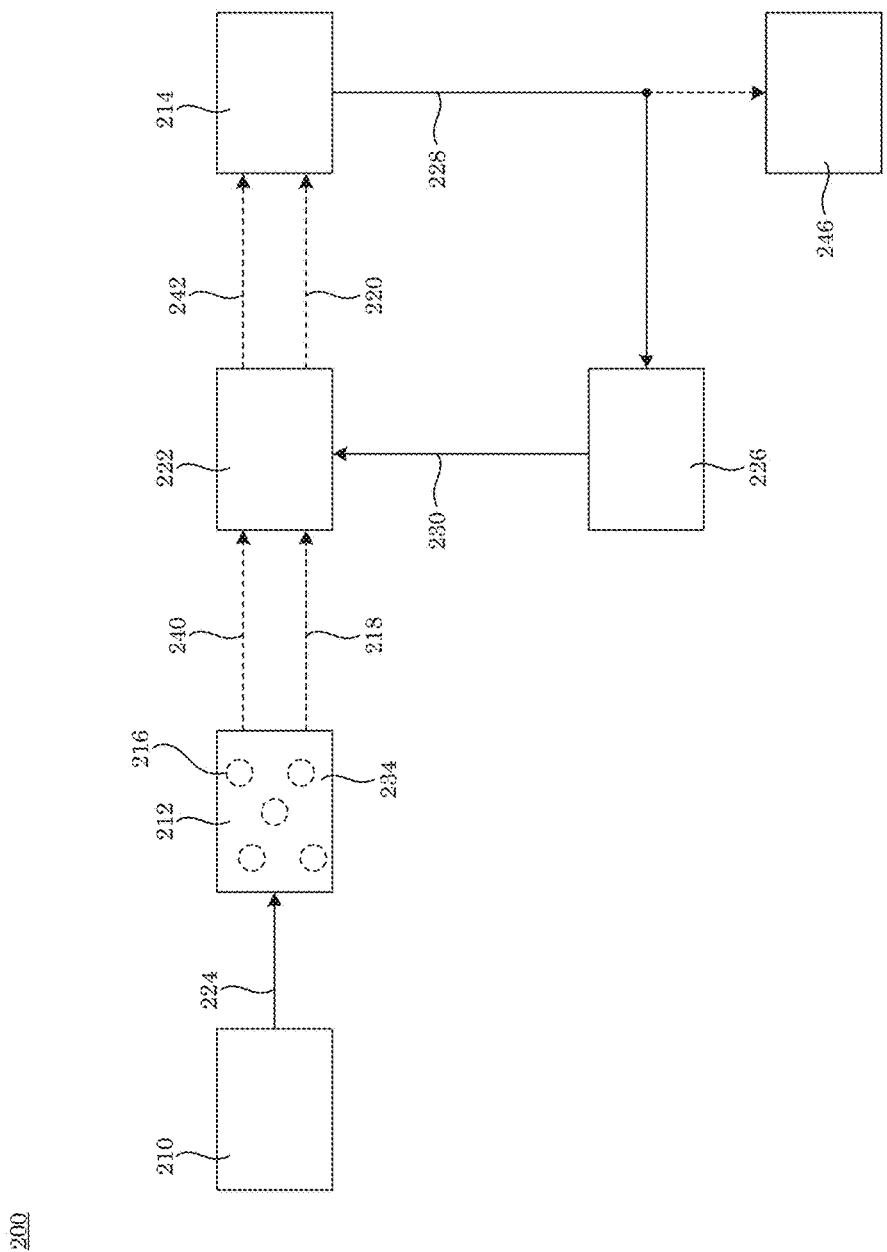
FIG. 2 shows a spectrum adjuster with a sample interposed between a light source and a dynamic opacity optic.

Spectrum adjuster 200 can include spectrum analyzer 246 in communication with detector 214. Spectrum adjuster 200 receives transmitted light signal 228 from detector 214 and determines pure analyte spectrum 232 of analyte 216. Moreover, as shown in FIG. 2, spectrum adjuster 200 can have sample 212 interposed between light source 210 and dynamic opacity optic 222.

It should be appreciated the spectrum adjuster 200 has modes of operation based on a presence or absence of analyte 216 in sample 212. When analyte 216 is disposed in sample 212, dynamic opacity optic 222 produces secondary adjusted light 218 and adjusts intensity of light in secondary adjusted light 218 as function of wavelength based on adjustment signal 230, which is based on transmitted light signal 228 from detector 214. When analyte 216 is absent in sample 212, dynamic opacity optic 222 produces primary adjusted light 240 and adjusts intensity of light in primary adjusted light 240 as function of wavelength based on adjustment signal 230, which is based on transmitted light signal 228 from detector 214. In this manner, dynamic opacity optic 222 selectively and dynamically adjusts secondary adjusted light 218 or primary adjusted light 240 as function of wavelength based on adjustment signal 230. It is contemplated that an intensity of secondary adjusted light 218 is increased at a wavelength when an absorption of sample 212 in an absence of analyte 216 is strongly absorbing of primary adjusted light 240. Strong absorption and variants of this term such as strongly absorptive, strong absorber, and the like can refer to an absorption that is greater than or equal to 80% of the primary adjusted light 240, specifically greater than or equal to 90% of the primary adjusted light 240, more specifically greater than or equal to 95% of the primary adjusted light 240, further specifically greater than or equal to 99% of the primary adjusted light 240, and further more specifically greater than or equal to 99.5% of the primary adjusted light 240.

Spectrum adjuster 200 produces adjusts an amount of light subjected to sample 212. Spectrum adjuster 200 includes light source 210 that can include components to generate incident light that can be transferred through a free space or through a set of optical components, such as lenses and fiber optics. In an embodiment, light source 210 includes external cavity quantum cascade lasers that generate mid-infrared light.

Light source 210 produces input light 224 that has an intensity as a function of wavelength. The wavelength can be from 200 nm to 20000 nm, specifically from 2500 nm to 10000 nm, and more specifically from 5700 nm to 6700 nm. An intensity of input light 224 can be characterized by optical power, which can be from 200 nm to 20000 nm, specifically from 2500 nm to 10000 nm, and more specifically from 5700 nm to 6700 nm. Moreover, input light 224 can produce monochromatic light or broadband continuum light and be operated as a pulsed mode or a continuous-wave mode. In an embodiment, input light 224 produces monochromatic light scanning from 6500 nm to 11000 nm in a pulsed mode with the bandwidth of 1 $cm^{-1}$, the repetition rate of 100 kHz, and the duty cycle of 5%.

Sample 212 can include matrix 234, analyte 216, or a combination thereof. Sample 212 can also include solvent and analytes that are dissolved in the solvent to measure the concentration of the analyte and can be solid matrix containing analytes that are dispersed in the matrix. In an embodiment, sample 212 includes an aqueous solution of protein.

Detector 214 can convert the light signal of secondary transmitted light 220 or primary transmitted light 242 into transmitted light signal 228. In an embodiment, detector 214 includes a mercury-cadmium-telluride detector, a pyroelectric detector, an indium arsenide detector, an indium antimonide detector, a silicon photodiode, an indium gallium arsenide detector, a photomultiplier, and the like.

Analyte 216 can be mixed with matrix 234 in sample 212. In an embodiment, analyte 216 includes protein, polymer, carbohydrate, mineral, and the like.

Secondary adjusted light 218 can be light transmitted by dynamic opacity optic 222 in response to adjustment signal 230. In an embodiment, secondary adjusted light 218 include infrared light, visible light, ultraviolet light, and the like.

Secondary transmitted light 220 can be secondary adjusted light 218 transmitted by sample 212 containing matrix 234 in the presence of analyte 216. In an embodiment, secondary transmitted light 220 includes infrared light, visible light, ultraviolet light, and the like.

Dynamic opacity optic 222 can modify transmission of input light 224 into primary adjusted light 240 or secondary adjusted light 218 based on adjustment signal 230. In an embodiment, dynamic opacity optic 222 includes an acousto-optic modulator, a spatial light modulator, a pre-programmed wavelength-dependent transmission optics, and the like.

Input light 224 can be generated by light source 210. In an embodiment, input light 224 includes infrared light, visible light, ultraviolet light, and the like.

Adjustment controller 226 can generate adjustment signal 230 based on transmitted light signal 228. In an embodiment, adjustment controller 226 includes a controller of an acousto-optic modulator, a spatial light modulator, a device that pre-programs wavelength-dependent transmission of an optics, and the like.

Transmitted light signal 228 can be generated by detector 214 in response to secondary transmitted light 220 or primary transmitted light 242. In an embodiment, transmitted light signal 228 includes electrical voltage, electrical current, light intensity, and the like.

Adjustment signal 230 can be generated by adjustment controller 226 in response to transmitted light signal 228. In an embodiment, adjustment signal 230 includes electrical voltage, electrical current, light intensity, and the like.

Pure analyte spectrum 232 can be generated by spectrum analyzer 246 in response to transmitted light signal 228. In an embodiment, pure analyte spectrum 232 includes a transmission spectrum, an absorption spectrum, a reflectance spectrum, an intensity spectrum, and the like.

Matrix 234 can be mixed with analyte 216 in sample 212. In an embodiment, matrix 234 includes a liquid solvent, hydrogel, vapor, solid matrix, and the like.

Primary adjusted light 240 can be light transmitted by dynamic opacity optic 222. In an embodiment, primary adjusted light 240 includes infrared light, visible light, ultraviolet light, and the like.

Primary transmitted light 242 can be primary adjusted light 240 transmitted by sample 212 containing matrix 234 in the absence of analyte 216. In an embodiment, primary transmitted light 242 includes infrared light, visible light, ultraviolet light, and the like.

Spectrum analyzer 246 can generate pure analyte spectrum 232 in response to transmitted light signal 228. In an embodiment, spectrum analyzer 246 includes a computer, a digital-to-analog converter, an oscilloscope, a recording device, and the like.

Spectrum adjuster 200 can be made in various ways. In an embodiment, a process for making spectrum adjuster 200 includes disposing light source 210 in optical communication with dynamic opacity optic 222; disposing adjustment controller 226 in electrical communication with dynamic opacity optic 222; disposing dynamic opacity optic 222 in communication with detector 214; and disposing detector 214 in communication with adjustment controller 226. Analyte 216 can be interposed between and in optical communication with dynamic opacity optic 222 and detector 214.

In the process for making spectrum adjuster 200, disposing light source 210 in optical communication with dynamic opacity optic 222 can include directing the light from light source 210 using mirrors and lenses in free space to dynamic opacity optic 222. Disposing light source 210 in optical communication with dynamic opacity optic 222 can also include attaching an optical fiber to a light outlet port of a laser that operates as light source 210 and connecting the free end of the optical fiber to dynamic opacity optic 222. In an embodiment, metallic mirrors direct the light from a laser to the input port of dynamic opacity optic 222.

In the process for making spectrum adjuster 200, disposing adjustment controller 226 in electrical communication with dynamic opacity optic 222 can include connecting electrical cables and optical fibers from adjustment controller 226 to dynamic opacity optic 222.

In the process for making spectrum adjuster 200, disposing dynamic opacity optic 222 in communication with detector 214 can include directing the light from dynamic opacity optic 222 using mirrors and lenses in free space to sample 212 and then directing the light from sample 212 using mirrors and lenses in the free space to detector 214. Disposing dynamic opacity optic 222 in communication with detector 214 can also include directing the light using fiber optics from dynamic opacity optic 222 to sample 212 and to detector 214. In an embodiment, light from dynamic opacity optic 222 is directed by a metallic mirrors to the transmission path of sample 212 and focused by a lens to the active area of detector 214.

In the process for making spectrum adjuster 200, disposing detector 214 in communication with spectrum analyzer 246 can include connecting electrical cables and optical fibers from detector 214 to spectrum analyzer 246.

In the process for making spectrum adjuster 200, disposing spectrum analyzer 246 in communication with adjustment controller 226 can include connecting electrical cables and optical fibers from spectrum analyzer 246 to adjustment controller 226.

In the process for making spectrum adjuster 200, interposing analyte 216 between and in optical communication with dynamic opacity optic 222 and detector 214 can include placing analyte 216 into sample 212 that is positioned between dynamic opacity optic 222 and detector 214. In an embodiment, a solution containing matrix 234 and analyte 216 replaces a solution containing only matrix 234 in the absence of analyte 216 in sample 212.

Sample 212 can be made by introducing a matrix or a combination of matrix and analyte in a sample containing a cell and locating the sample in optical communication between dynamic opacity optic 222 and detector 214.

Making individual components of spectrum adjuster 200 can be accomplished using, e.g., additive manufacturing, mechanical machining, and the like. Components can be joined together by mechanical joints, chemical adhesives, and free contacts. Alignment of individual components can be performed by automatic feedback or manually.

It is contemplated that making spectrum adjuster 200 can include a process by which dynamic opacity optic 222 with a fixed transmission is produced at a remote site, received by a user, and subsequently used to obtain secondary transmitted light 220 and pure analyte spectrum 232. In an embodiment, a process for making dynamic opacity optic 222 with a fixed transmission at a remote site includes disposing light source 210 in optical communication with dynamic opacity optic 222; disposing adjustment controller 226 in electrical communication with dynamic opacity optic 222; disposing dynamic opacity optic 222 in communication with detector 214; disposing detector 214 in communication with adjustment controller 226; interposing sample 212 containing matrix 234 between and in optical communication with dynamic opacity optic 222 and detector 214.

Spectrum adjuster 200 produces secondary adjusted light 218. In an embodiment, a process for producing secondary adjusted light 218 includes: producing input light 224; receiving, by dynamic opacity optic 222, input light 224;

producing, by dynamic opacity optic 222, primary adjusted light 240 from input light 224; subjecting sample 212 in absence of analyte 216 to primary adjusted light 240; communicating, from sample 212, primary transmitted light 242, in response to subjecting sample 212 in absence of analyte 216 to primary adjusted light 240; receiving, by detector 214, primary transmitted light 242; producing, by detector 214, transmitted light signal 228 based on primary transmitted light 242; receiving, by adjustment controller 226, transmitted light signal 228 from detector 214; producing, by adjustment controller 226, adjustment signal 230 based on transmitted light signal 228; communicating adjustment signal 230 from adjustment controller 226 to dynamic opacity optic 222; and producing, by dynamic opacity optic 222, secondary adjusted light 218 based on adjustment signal 230 to produce secondary adjusted light 218.

In the process for producing secondary adjusted light 218, producing input light 224 can include generating light from light source 210 and controlling conditions of the light including wavelength, intensity, and bandwidth.

In the process for producing secondary adjusted light 218, receiving, by dynamic opacity optic 222, input light 224 can include transmitting, refracting, and reflecting input light 224 by reflective and refractive optical components in free space or by optical fibers to the entrance of dynamic opacity optic 222.

In the process for producing secondary adjusted light 218, producing, by dynamic opacity optic 222, primary adjusted light 240 from input light 224 can include transmitting input light 224 by controlling the direction and divergence of primary adjusted light 240.

In the process for producing secondary adjusted light 218, subjecting sample 212 containing matrix 234 in absence of analyte 216 to primary adjusted light 240 can include inserting sample 212 containing matrix 234 in absence of analyte 216 into the path of optical communication between dynamic opacity optic 222 and detector 214. In an embodiment, a liquid cell containing solvent without analyte can be inserted in the beam path between dynamic opacity optic 222 and detector 214.

In the process for producing secondary adjusted light 218, communicating, from sample 212, primary transmitted light 242, in response to subjecting sample 212 in absence of analyte 216 to primary adjusted light 240, can include transmitting, refracting, and reflecting primary transmitted light 242 to detector 214 by using refractive and reflective optical components.

In the process for producing secondary adjusted light 218, receiving, by detector 214, primary transmitted light 242 can include converting the optical power of primary transmitted light 242 into an electronic signal. In an embodiment, a mercury-cadmium-telluride detector converts infrared light intensity into an electronic voltage signal.

In the process for producing secondary adjusted light 218, producing, by detector 214, transmitted light signal 228 based on primary transmitted light 242 can include generating electronic, optical, and wireless signals in response to primary transmitted light 242.

In the process for producing secondary adjusted light 218, receiving, by adjustment controller 226, transmitted light signal 228 from detector 214 can include receiving transmitted light signal 228 as an electronic signal, optical signal, or wireless signal that can be converted to adjustment signal 230.

In the process for producing secondary adjusted light 218, producing, by adjustment controller 226, adjustment signal 230 based on transmitted light signal 228 can include transmitting electronic, optical, and wireless signals to dynamic opacity optic 222.

In the process for producing secondary adjusted light 218, communicating adjustment signal 230 from adjustment controller 226 to dynamic opacity optic 222 can include transmitting electronic, optical, and wireless signals that can control dynamic opacity optic 222.

In the process for producing secondary adjusted light 218, producing, by dynamic opacity optic 222, secondary adjusted light 218 based on adjustment signal 230 can include controlling transmission of dynamic opacity optic 222 to a selected intensity of secondary adjusted light 218. In an embodiment, an acousto-optic modulator transmits light of different wavelengths with transmissions that is differently adjusted by the controlling signal from adjustment controller 226.

In the process for producing secondary adjusted light 218, controlling intensity of secondary adjusted light 218 based on adjustment signal 230 can include increasing, by dynamic opacity optic 222, intensity of secondary adjusted light 218 relative to an intensity of primary adjusted light 240 at wavelength of input light 224 at which sample 212 in absence of analyte 216 absorbs greater than or equal to 80% of primary adjusted light 240. It is contemplated that this is accomplished by increasing the transmission of dynamic opacity optic 222.

In the process for producing secondary adjusted light 218, controlling intensity of secondary adjusted light 218 based on adjustment signal 230 can also include decreasing, by dynamic opacity optic 222, intensity of secondary adjusted light 218 relative to an intensity of primary adjusted light 240 at wavelength of input light 224 at which sample 212 in absence of analyte 216 transmits greater than or equal light intensity of the detection limit of detector 214. It is contemplated that this is accomplished by decreasing the transmission of dynamic opacity optic 222.

In an embodiment, a process for producing pure analyte spectrum 232 includes: producing input light 224; receiving, by dynamic opacity optic 222, input light 224; producing, by dynamic opacity optic 222, primary adjusted light 240 from input light 224; subjecting sample 212 in absence of analyte 216 to primary adjusted light 240; communicating, from sample, primary transmitted light 242, in response to subjecting sample 212 in absence of analyte 216 to primary adjusted light 240; receiving, by detector 214, primary transmitted light 242; producing, by detector 214, transmitted light signal 228 based on primary transmitted light 242; receiving, by adjustment controller 226, transmitted light signal 228 from detector 214; producing, by adjustment controller 226, adjustment signal 230 based on transmitted light signal 228; communicating adjustment signal 230 from adjustment controller 226 to dynamic opacity optic 222; and producing, by dynamic opacity optic 222, secondary adjusted light 218 based on adjustment signal 230; subjecting sample 212 comprising analyte 216 to secondary adjusted light 218; communicating, from sample 212, secondary transmitted light 220 in response to subjecting sample 212 in presence of analyte 216 to primary adjusted light 240; receiving, by detector 214, secondary transmitted light 220; producing, by detector 214, transmitted light signal 228 based on secondary transmitted light 220; receiving, by spectrum analyzer 246, transmitted light signal 228 from detector 214; and converting transmitted light signal 228 into pure analyte spectrum 232 to produce pure analyte spectrum 232.

The process for producing pure analyte spectrum 232 can include controlling an intensity of secondary adjusted light 218 based on adjustment signal 230. In the process for producing pure analyte spectrum 232, controlling intensity of secondary adjusted light 218 based on adjustment signal 230 can include increasing, by dynamic opacity optic 222, intensity of secondary adjusted light 218 relative to an intensity of primary adjusted light 240 at a wavelength of input light 224 at which sample 212 in absence of analyte 216 absorbs greater than or equal to 80% of primary adjusted light 240.

It is contemplated that in the process for producing pure analyte spectrum 232, producing input light 224 can include generating light from light source 210 and controlling conditions of the light including wavelength, intensity, and bandwidth.

In the process for producing pure analyte spectrum 232, receiving, by dynamic opacity optic 222, input light 224 can include transmitting, refracting, and reflecting input light 224 by reflective and refractive optical components in free space or by optical fibers to the entrance of dynamic opacity optic 222.

In the process for producing pure analyte spectrum 232, producing, by dynamic opacity optic 222, primary adjusted light 240 from input light 224 can include transmitting input light 224 by controlling the direction and divergence of primary adjusted light 240.

In the process for producing pure analyte spectrum 232, subjecting sample 212 containing matrix 234 in absence of analyte 216 to primary adjusted light 240 can include inserting sample 212 containing matrix 234 in absence of analyte 216 into the path of optical communication between dynamic opacity optic 222 and detector 214. In an embodiment, a liquid cell containing solvent without analyte can be inserted in the beam path between dynamic opacity optic 222 and detector 214.

In the process for producing pure analyte spectrum 232, communicating, from sample, primary transmitted light 242, in response to subjecting sample 212 in absence of analyte 216 to primary adjusted light 240 can include transmitting, refracting, and reflecting primary transmitted light 242 to detector 214 by using refractive and reflective optical components.

In the process for producing pure analyte spectrum 232, receiving, by detector 214, primary transmitted light 242 can include measuring the intensity of primary transmitted light 242. In an embodiment, a mercury-cadmium-telluride detector converts infrared light intensity into an electronic voltage signal.

In the process for producing pure analyte spectrum 232, producing, by detector 214, transmitted light signal 228 based on primary transmitted light 242 can include generating electronic, optical, and wireless signals in response to primary transmitted light 242.

In the process for producing pure analyte spectrum 232, receiving, by adjustment controller 226, transmitted light signal 228 from detector 214 can include receiving transmitted light signal 228 in the forms of electronic, optical, and wireless signals that can be translated into adjustment signal 230.

In the process for producing pure analyte spectrum 232, producing, by adjustment controller 226, adjustment signal 230 based on transmitted light signal 228 can include transmitting electronic, optical, and wireless signals to dynamic opacity optic 222.

In the process for producing pure analyte spectrum 232, communicating adjustment signal 230 from adjustment controller 226 to dynamic opacity optic 222 can include transmitting electronic, optical, and wireless signals that can control dynamic opacity optic 222.

In the process for producing pure analyte spectrum 232, producing, by dynamic opacity optic 222, secondary adjusted light 218 based on adjustment signal 230 can include controlling transmission of dynamic opacity optic 222 to intended intensity of secondary adjusted light 218. In an embodiment, an acousto-optic modulator transmits light of different wavelengths with transmissions that is differently adjusted by the controlling signal from adjustment controller 226.

In the process for producing pure analyte spectrum 232, subjecting sample 212 including matrix 234 and analyte 216 to secondary adjusted light 218 can include inserting sample 212 into the path of optical communication of secondary adjusted light 218. In an embodiment, a liquid cell containing solvent and analyte can be inserted in the beam path of secondary adjusted light 218 between dynamic opacity optic 222 and detector 214.

In the process for producing pure analyte spectrum 232, communicating, from sample 212, secondary transmitted light 220 in response to subjecting sample 212 in presence of analyte 216 to secondary adjusted light 218 can include transmitting, refracting, and reflecting primary transmitted light 242 to detector 214 by using refractive and reflective optical components.

In the process for producing pure analyte spectrum 232, receiving, by detector 214, secondary transmitted light 220 can include converting the optical power of primary transmitted light 242 into an electronic signal. In an embodiment, a mercury-cadmium-telluride detector converts infrared light intensity into an electronic voltage signal.

In the process for producing pure analyte spectrum 232, producing, by detector 214, transmitted light signal 228 based on secondary transmitted light 220 can include generating electronic, optical, and wireless signals in response to secondary transmitted light 220.

In the process for producing pure analyte spectrum 232, receiving, by spectrum analyzer 246, transmitted light signal 228 from detector 214 can include receiving transmitted light signal 228 in the forms of electronic, optical, and wireless signals.

In the process for producing pure analyte spectrum 232, converting transmitted light signal 228 into pure analyte spectrum 232 can include analyzing the received signal by spectrum analyzer 246 and converting the signal into a quantity that can be used to make pure analyte spectrum 232. In an embodiment, electronic signals generated by a mercury-cadmium-telluride detector as a function of wavelength are converted into a transmission spectrum of an analyte.

Figure 3:
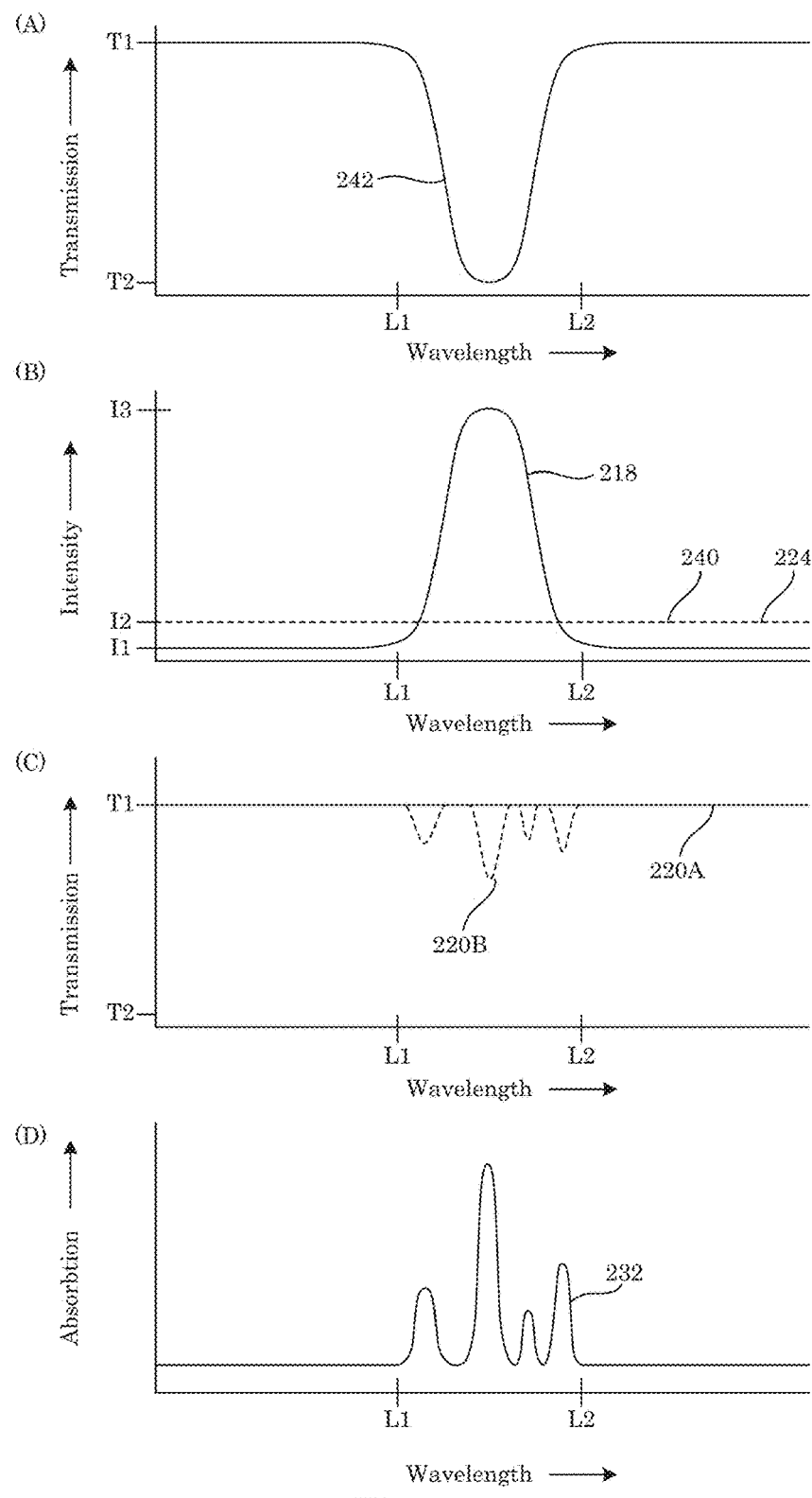
FIG. 3 shows a graph of transmission versus wavelength in panel A, a graph of intensity versus wavelength in panel B, a graph of transmission versus wavelength in panel C, and a graph of absorption versus wavelength in panel D.

According to an embodiment, with reference to FIG. 3, a process for producing pure analyte spectrum 232 includes subjecting sample 212 in an absence of analyte 216 with primary adjusted light 240 that is substantially a same intensity as input light 224 with intensity 12 as shown in panel B such that sample 212 in an absence of analyte 216 has a transmission as a function of wavelength shown in panel A. Here, the transmission decreases from first transmission T1 at first wavelength L1 to second transmission T2 between first wavelength L1 and second wavelength L2 and increases from second transmission T2 toward first transmission T1 at second wavelength L2. Thereafter, dynamic opacity optic 222 receives adjustment signal 230 and produces secondary adjusted light 218 based on adjustment signal 230 so that secondary adjusted light 218 has the nonuniform intensity profile as a function of wavelength shown in panel B, wherein an intensity of secondary adjusted light 218 counteracts the drop in transmission due to absorption of sample 212 in an absence of analyte 216 from first wavelength L1 and second wavelength L2. Here, dynamic opacity optic 222 produces secondary adjusted light 218 based on adjustment signal 230 so that an intensity of secondary adjusted light 218 increases from first intensity I1 at first wavelength L1 to third intensity 13 between first wavelength L1 and second wavelength L2, and decreases from third intensity 13 toward first intensity I1 at second wavelength L2. Accordingly, as shown in panel C, when sample 212 in an absence of analyte 216 is subjected to secondary adjusted light 218, a transmission is uniform and has a transmission profile shown as secondary transmitted light 220A. When analyte 216 is present in sample 212 and subjected to secondary adjusted light 218, a transmission from sample 212 is shown as secondary transmitted light 220B in panel C. That is, due to secondary adjusted light 218, the transmission spectrum of sample 212 is uniform according to secondary transmitted light 220A for absence of analyte 216 or not uniform according to secondary transmitted light 220B for presence of analyte 216 where, e.g., the four features present for secondary transmitted light 220B that have lower transmission than first transmission T1 from first wavelength L1 to second wavelength L2 are due to absorption of secondary adjusted light 218 by analyte 216. Data shown in panel C can be communicated as transmitted light signal 228 from detector 214 to spectrum analyzer 246, wherein spectrum analyzer 246 analyzes transmitted light signal 228 and produces pure analyte spectrum 232 shown in panel D from secondary transmitted light 220 communicated within transmitted light signal 228 and received by spectrum analyzer 246.

Spectrum adjuster 200 and processes disclosed herein have numerous beneficial uses, including enhancing absorption measurement sensitivity, increasing the optical path length, reducing the contribution of variable path length of demountable cells, and suppressing the water vapor contribution to the measured transmission spectrum. Advantageously, spectrum adjuster 200 overcomes limitations of technical deficiencies of conventional articles, e.g., transmission spectrometers, that include, e.g., a variation in pathlength in a detachable cell, a contribution of air humidity, a requirement for gas purge or sparging, a contribution to absorption of a deposit on a cell window, a limited concentration sensitivity to analytes, and the like. Further, a typical path length variation of approximately 1 micrometer can produce uncertainty in mid-infrared transmission measurements for which a mean path length is shorter than 6 micrometers for conventional demountable cells for holding aqueous solutions. Increasing the optical path length to 50 micrometers by adjusting the incident light spectrum can reduce the contribution of the optical cell bowing from 17% to 2%.

Figure 4:
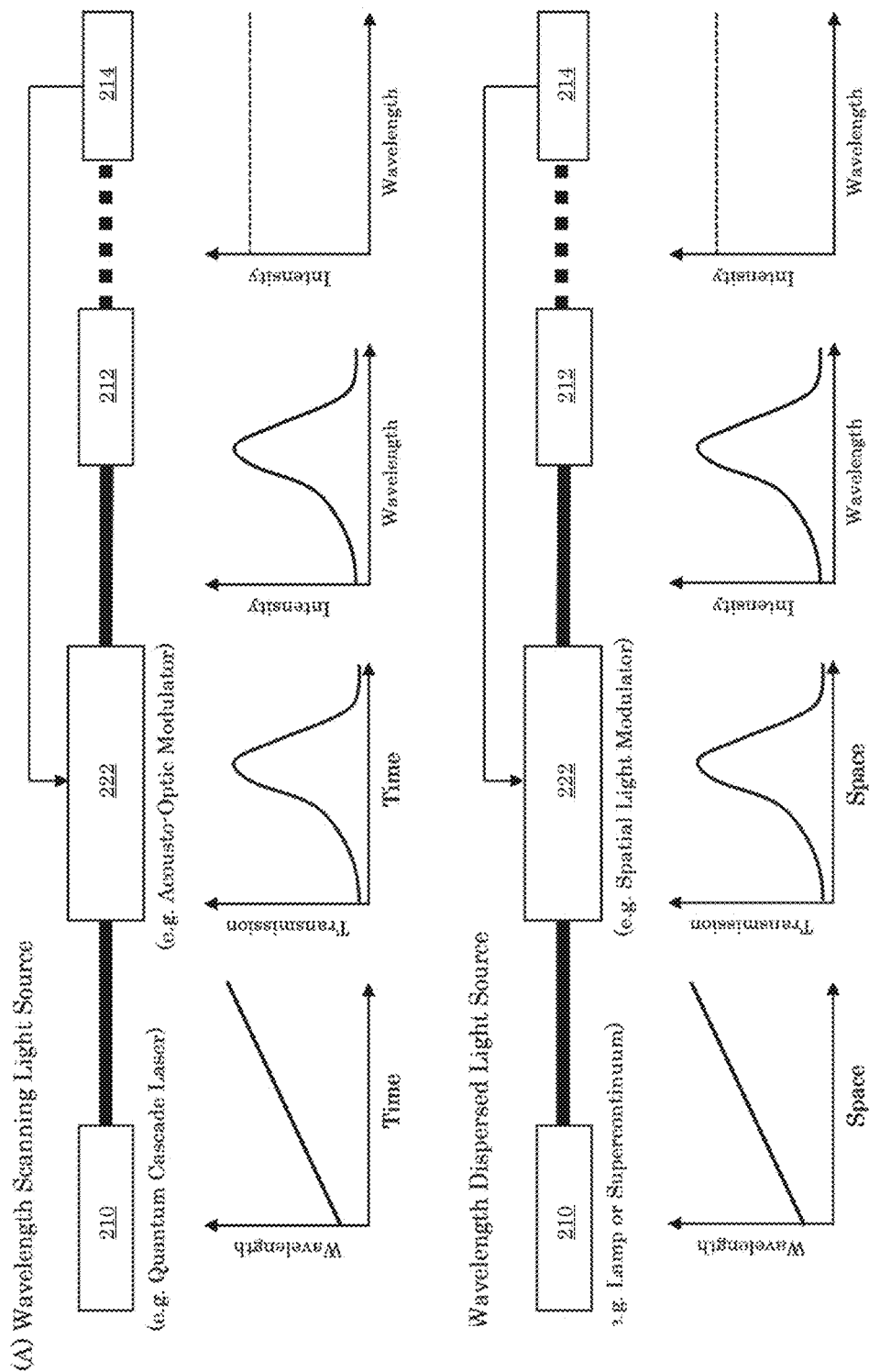
FIG. 4 shows embodiments of a spectrum adjuster in panel A and panel B.
Figure 5:
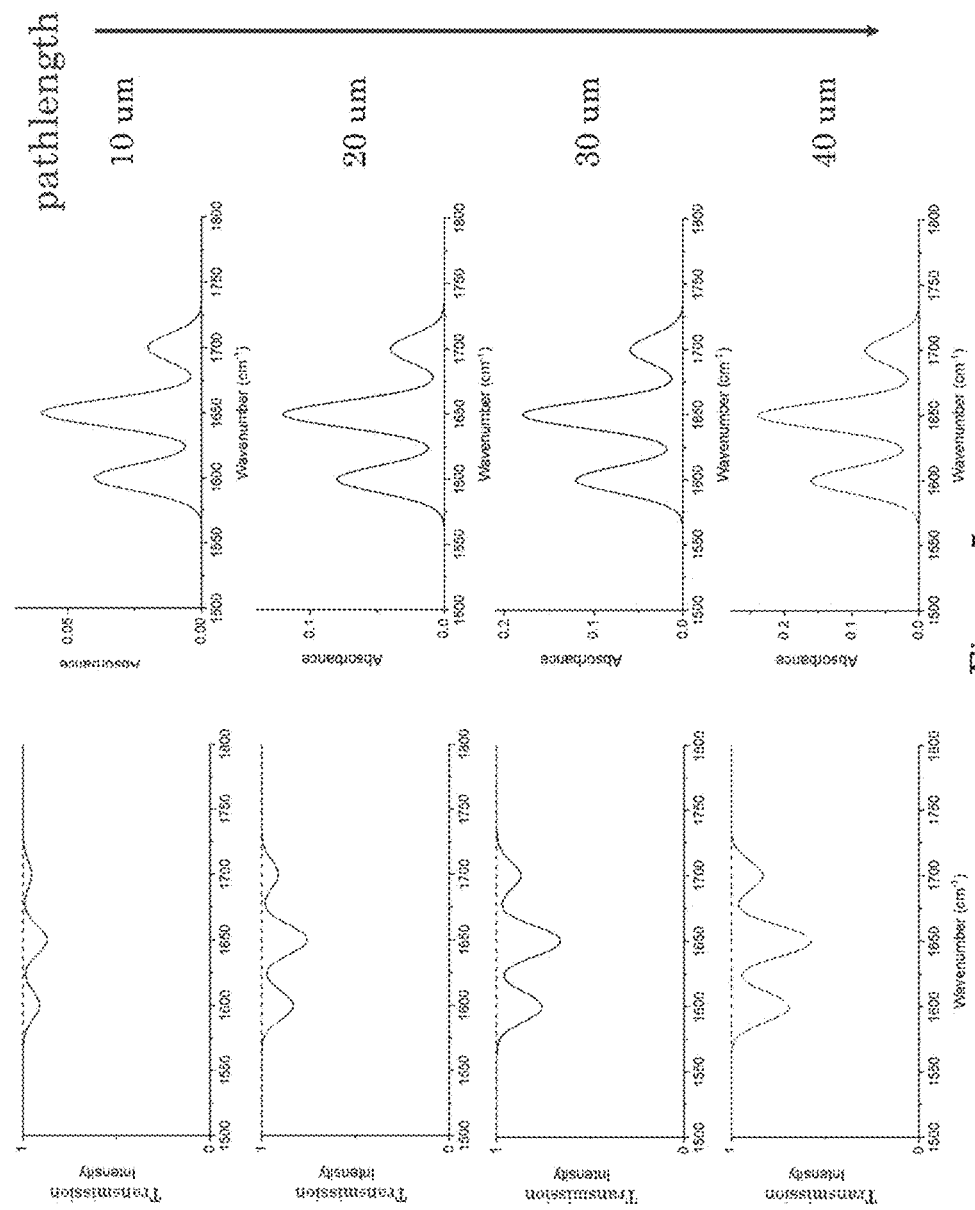
FIG. 5 shows graphs of transmission intensity versus wavenumber and graphs of absorbance versus wavenumber for a plurality of pathlengths from 10 μm to 40 μm.
Figure 6:
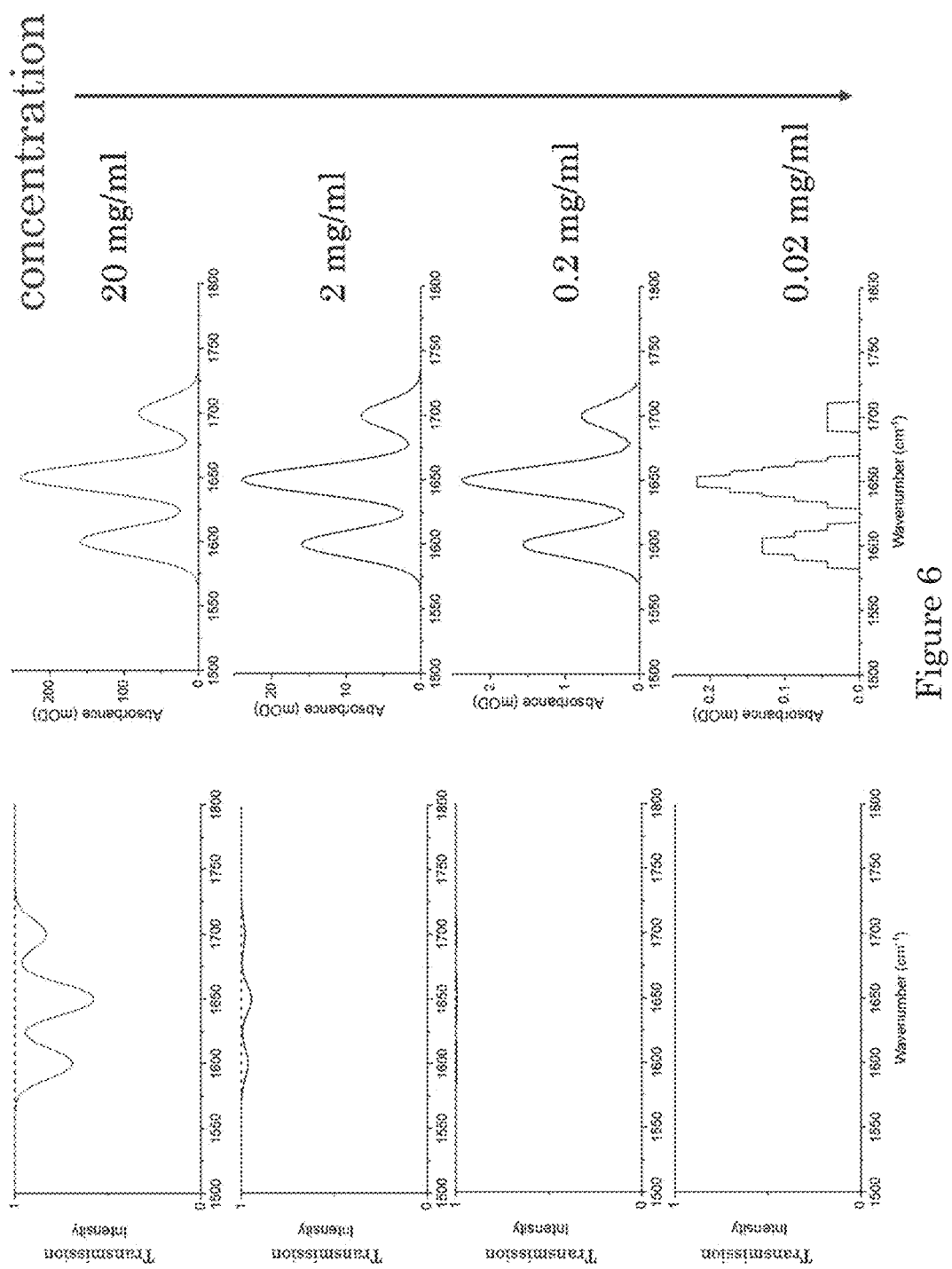
FIG. 6 shows graphs of transmission intensity versus wavenumber and graphs of absorbance versus wavenumber for a plurality of concentrations of an analyte from 20 mg/mL to 0.02 mg/mL.

Exemplary embodiments for spectrum adjuster 200 are shown in panel A and panel B of FIG. 4. By selectively removing the contribution of matrix 234, spectrum adjuster 200 uses the dynamic range of detector 214 only for analyte 216. It is contemplated that spectrum adjuster 200 provides an advantage over conventional spectrometers with respect to pathlength such that a longer pathlength can be used to contain sample 212 that overcomes a limited dynamic range imposed by a thicker pathlength, wherein exemplary data from spectrum adjuster 200 is shown in FIG. 5. It also is contemplated that spectrum adjuster 200 provides an advantage over conventional spectrometers with respect to concentration of the analyte in the sample such that a smaller concentration of analyte can be used in sample 212 that overcomes having to have a greater concentration of analyte in conventional spectrometers due to strong absorption by a matrix in which the analyte is disposed, wherein exemplary data from spectrum adjuster 200 for a plurality of concentration of an analyte is shown in FIG. 6.

Moreover, spectrum adjuster 200 and processes herein have numerous advantageous properties. In an aspect, higher sensitivity can be obtained by adjusting the incident light spectrum that can be used to determine a structure of protein that is at a low concentration, e.g., vaccines, protein cancer drugs. In addition, a conventional short pathlength does not allow for microfluidic introduction of liquid samples due to excessive pressure involved. An increased pathlength provided by adjusting the incident light spectrum can be used in microfluidic applications, which can furthermore be used for in-line/on-line characterization of process analytical technology (PAT); significantly lowers the detection limit of protein or other biomolecules in aqueous solutions that exist only at a low concentration.

Spectrum adjuster 200 and processed herein provide higher sensitivity, lower cost, longer pathlength, smaller amount of analyte 216 usage than conventional techniques and instruments such as FT-IR, QCL-IR, and the like.

The articles and processes herein are illustrated further by the following Example, which is non-limiting.

Example

Figure 7:
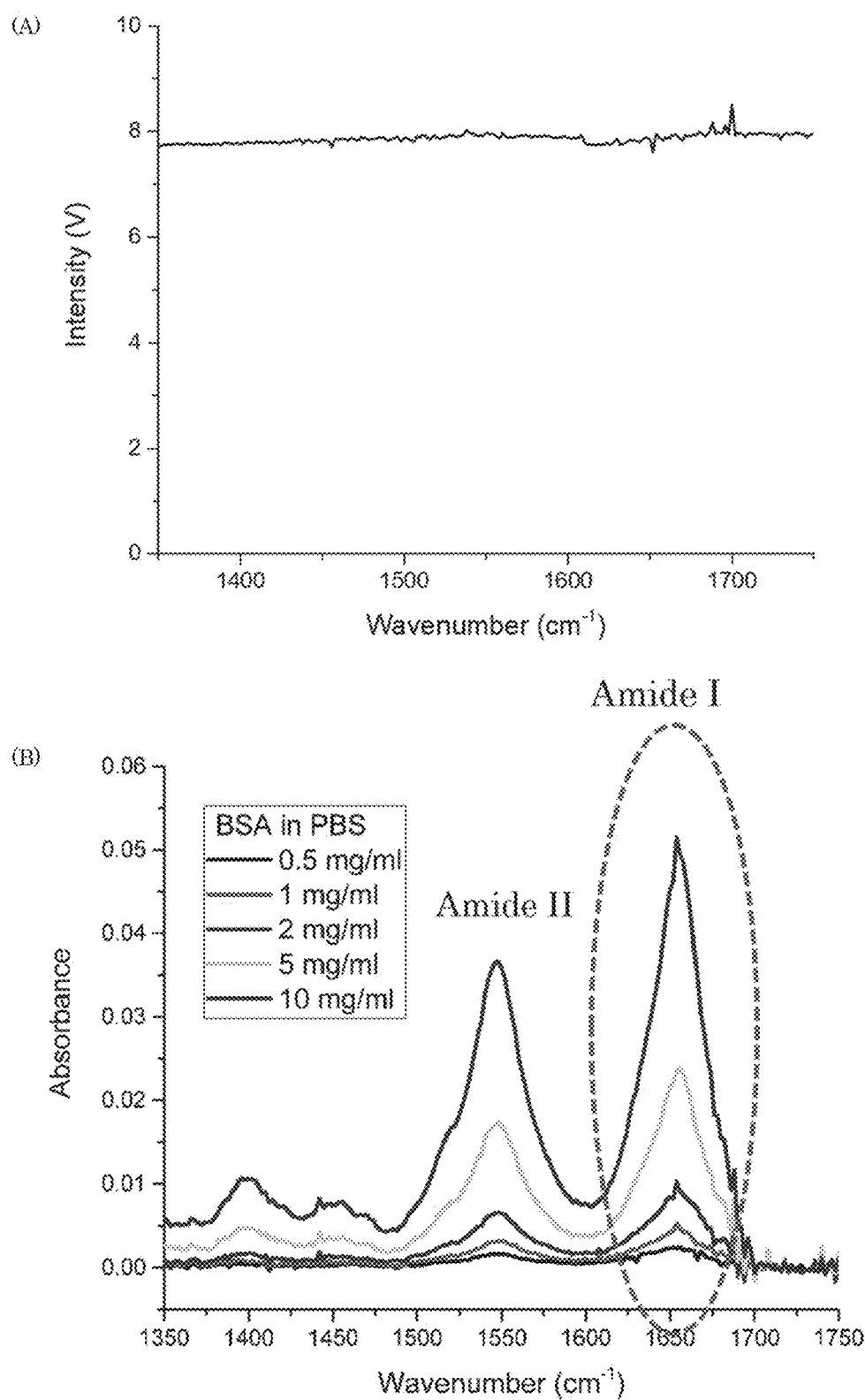
FIG. 7 shows a graph of transmitted light intensity versus wavenumber in panel A and a graph of absorbance versus wavenumber in panel B.
Figure 8:
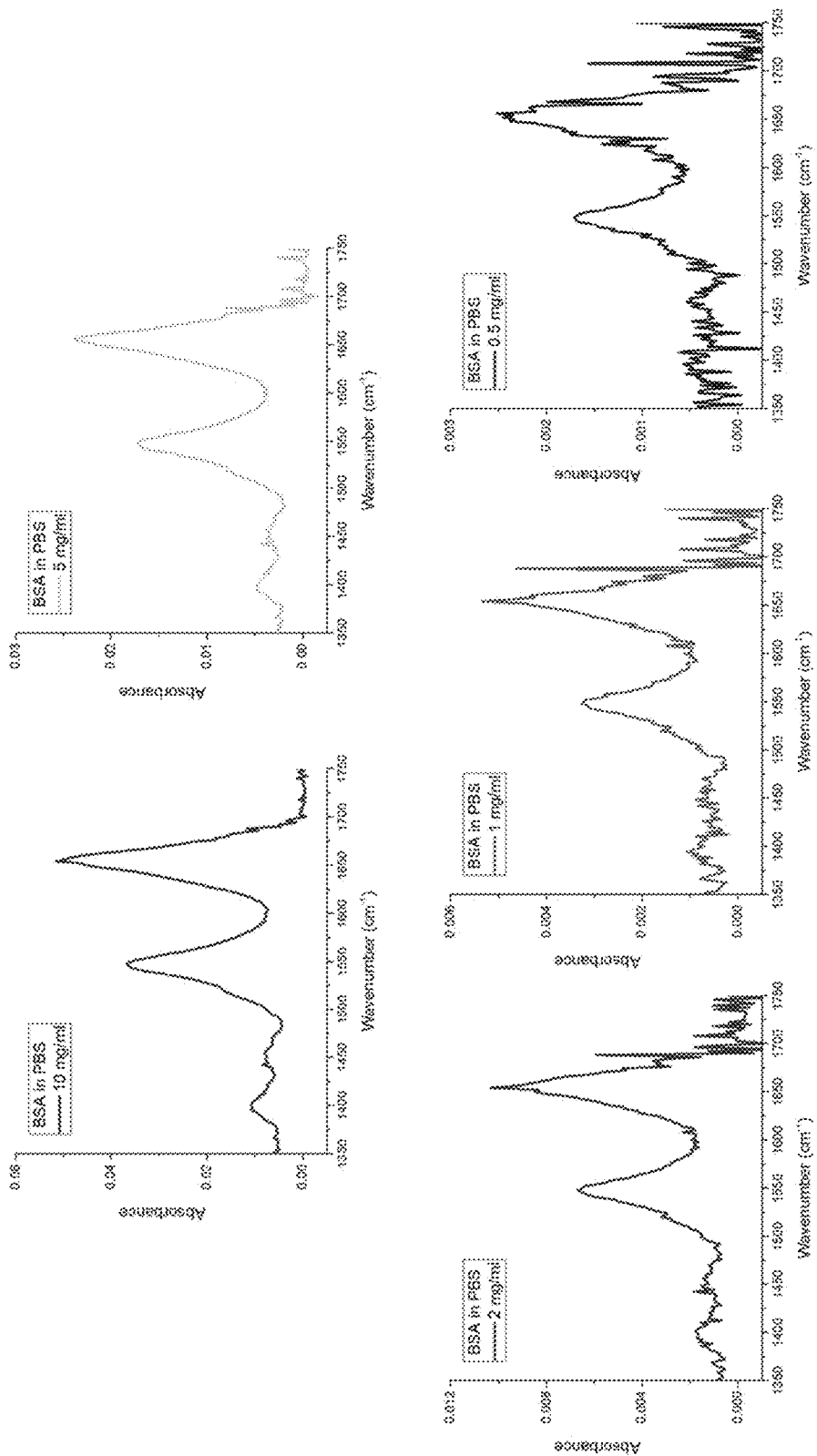
FIG. 8 shows graphs of absorbance versus wavenumber for the data shown in panel B of FIG. 7.

A spectrum adjuster was used to acquire a secondary transmitted light from which a pure analyte spectrum was determined. Here, the spectrum adjuster included an acousto-optic modulator that controlled the transmission of light while the wavelength of a mid-infrared laser was scanned. The sample without analyte was a phosphate-buffered saline solution. The transmission spectrum of secondary transmitted light for the sample in absence of an analyte is shown in panel A of FIG. 7 and was obtained by a mercury-cadmium-telluride detector and a boxcar signal processing system, which transferred a transmission spectrum to a computer that recorded the spectrum. Five new samples, each containing a different concentration of bovine serum albumin as the analyte, were prepared by dissolving the albumin into a phosphate-buffered saline solution. Transmission spectra for the five samples were acquired by the same mercury-cadmium-telluride detector and the same boxcar signal processing system and subjected to a liquid cell with calcium fluoride windows to obtain the absorption spectra shown in panel B of FIG. 7. The absorption spectrum is unaltered from 1600 $cm^{-1}$ to 1700 $cm^{-1}$ due to relatively high absorption of the analyte over the large background absorption of the water in the phosphate-buffered saline solution due to use of secondary adjusted light to acquire secondary transmitted light from the analyte in the matrix. FIG. 8 shows individual graphs of absorbance versus wavenumber for each of the different concentrations of the analyte the appear in the data shown in panel B of FIG. 7.

Comparative Example

Figure 9:
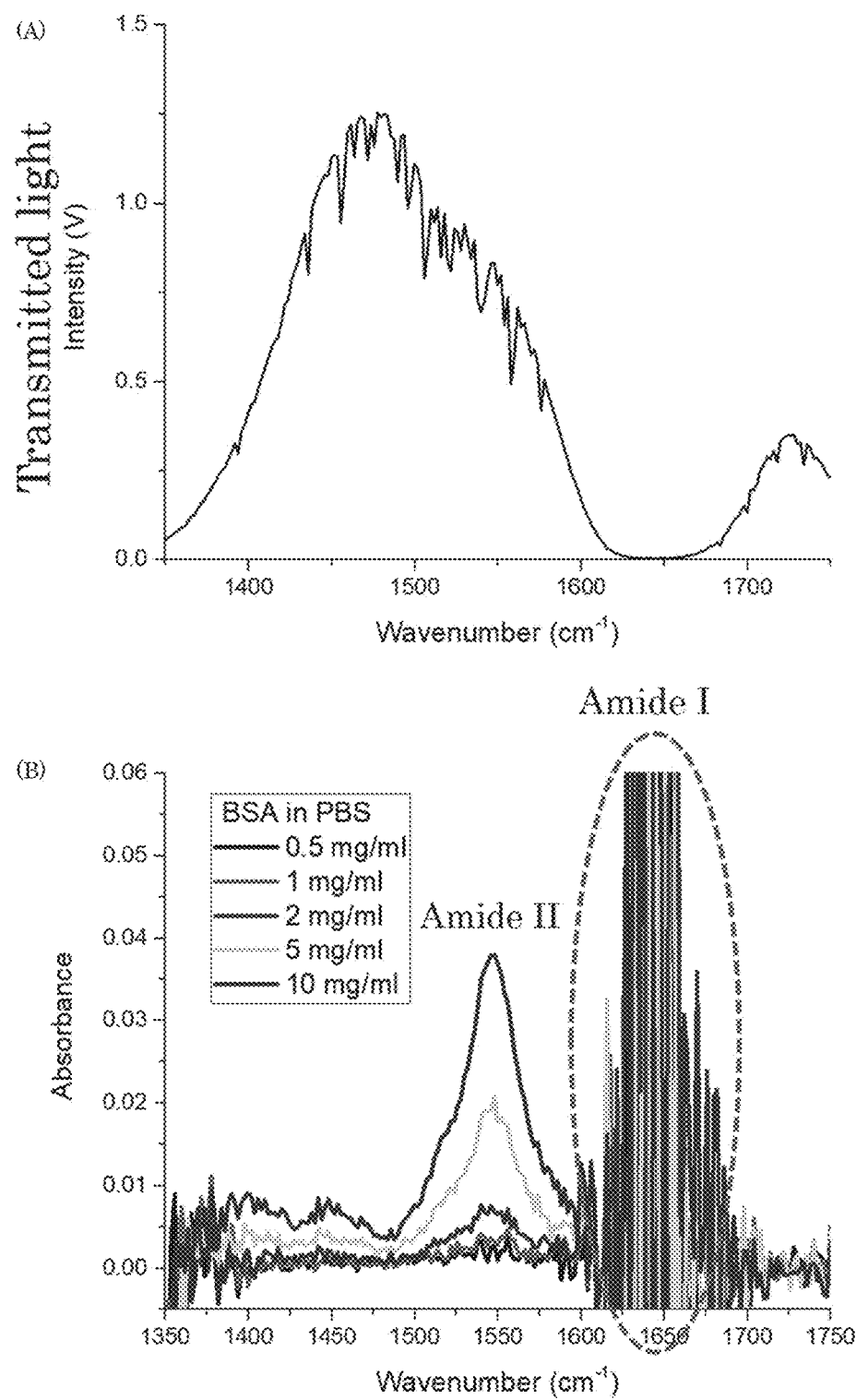
FIG. 9 shows a graph of transmitted light intensity versus wavenumber in panel A and a graph of absorbance versus wavenumber in panel B.

A conventional spectrometer was used to acquire a transmission spectrum from which an absorption spectrum was determined. Here, the conventional spectrometer included a wavelength scanning mid-infrared laser, a liquid cell with calcium fluoride windows, a mercury-cadmium-telluride detector, and a boxcar signal processing system. The sample in absence of an analyte was a phosphate-buffered saline solution. The transmission spectrum for the phosphate-buffered saline solution is shown in panel A of FIG. 9 and was obtained by the mercury-cadmium-telluride detector and the boxcar signal processing system. The transmission spectrum of five samples, each containing a different concentration of bovine serum albumin, was disposed in the liquid cell with calcium fluoride windows to obtain the absorption spectrum shown in panel B of FIG. 9. The absorption spectrum is extremely noisy from 1600 cm$^{-1}$ to 1700 cm$^{-1}$ due to high absorption by water of the phosphate-buffered saline solution in accord with the low transmission in this spectral region as shown in panel A.

What is claimed is:

1. A spectrum adjuster to produce a pure analyte spectrum of a sample, the spectrum adjuster comprising:
   a dynamic opacity optic that:
      receives input light;
      receives an adjustment signal;
      produces primary adjusted light from the input light based on the adjustment signal such that an intensity of the primary adjusted light is based on an amount of primary transmitted light transmitted through the sample in an absence of an analyte; and
      produces secondary adjusted light from the input light based on the adjustment signal such that an intensity of the secondary adjusted light is based on an amount of secondary transmitted light transmitted through the sample in a presence of the analyte;
   a light source in optical communication with the dynamic opacity optic and that communicates the input light to the dynamic opacity optic;
   a detector in optical communication with the dynamic opacity optic and that:
      receives transmitted light from the sample; and
      produces a transmitted light signal based on an amount of transmitted light received from the sample; and
   an adjustment controller in communication with the detector and the dynamic opacity optic and that:
      receives the transmitted light signal from the detector;
      produces the adjustment signal based on the transmitted light signal; and
      communicates the adjustment signal to the dynamic opacity optic,
   the dynamic opacity optic being optically interposed between the light source and the detector, and the sample when present being optically interposed between the dynamic opacity optic and the detector.

2. The spectrum adjuster of claim 1, further comprising a spectrum analyzer in communication with the detector and that:
   receives the transmitted light signal from the detector; and
   determines the pure analyte spectrum of the analyte.

3. The spectrum adjuster of claim 1, wherein the dynamic opacity optic controls an intensity of the secondary adjusted light based on the adjustment signal.

4. The spectrum adjuster of claim 3, wherein the dynamic opacity optic increases the intensity of the secondary adjusted light relative to an intensity of the primary adjusted light at a wavelength of the input light at which the sample in absence of the analyte absorbs greater than or equal to 80% of the primary adjusted light.

5. A process for producing a secondary adjusted light, the process comprising:
   producing an input light;
   receiving, by a dynamic opacity optic, the input light;
   producing, by the dynamic opacity optic, a primary adjusted light from the input light;
   subjecting a sample in an absence of an analyte to the primary adjusted light;
   communicating, from the sample, primary transmitted light, in response to subjecting the sample in the absence of the analyte to the primary adjusted light;
   receiving, by a detector, the primary transmitted light;
   producing, by the detector, a transmitted light signal based on the primary transmitted light;
   receiving, by an adjustment controller, the transmitted light signal from the detector;
   producing, by the adjustment controller, an adjustment signal based on the transmitted light signal;
   communicating the adjustment signal from the adjustment controller to the dynamic opacity optic; and
   producing, by the dynamic opacity optic, a secondary adjusted light based on the adjustment signal to produce the secondary adjusted light.

6. The process of claim 5, further comprising:
   controlling an intensity of the secondary adjusted light based on the adjustment signal.

7. The process of claim 6, wherein controlling the intensity of the secondary adjusted light based on the adjustment signal comprises:
   increasing, by the dynamic opacity optic, the intensity of the secondary adjusted light relative to an intensity of the primary adjusted light at a wavelength of the input light at which the sample in absence of the analyte absorbs greater than or equal to 80% of the primary adjusted light.

8. A process for producing a pure analyte spectrum, the process comprising:
   producing an input light;
   receiving, by a dynamic opacity optic, the input light;
   producing, by the dynamic opacity optic, a primary adjusted light from the input light;
   subjecting a sample in an absence of an analyte to the primary adjusted light;
   communicating, from the sample, primary transmitted light, in response to subjecting the sample in the absence of the analyte to the primary adjusted light;
   receiving, by a detector, the primary transmitted light;
   producing, by the detector, a transmitted light signal based on the primary transmitted light;
   receiving, by an adjustment controller, the transmitted light signal from the detector;
   producing, by the adjustment controller, an adjustment signal based on the transmitted light signal;
   communicating the adjustment signal from the adjustment controller to the dynamic opacity optic; and
   producing, by the dynamic opacity optic, a secondary adjusted light based on the adjustment signal;
   subjecting the sample comprising the analyte to the secondary adjusted light;
   communicating, from the sample, secondary transmitted light in response to subjecting the sample in presence of the analyte to the primary adjusted light;
   receiving, by the detector, the secondary transmitted light;
   producing, by the detector, the transmitted light signal based on the secondary transmitted light;
   receiving, by a spectrum analyzer, the transmitted light signal from the detector; and
   converting the transmitted light signal into the pure analyte spectrum to produce the pure analyte spectrum.

9. The process of claim 7, further comprising:
   controlling an intensity of the secondary adjusted light based on the adjustment signal.

10. The process of claim 8, wherein controlling the intensity of the secondary adjusted light based on the adjustment signal comprises:

increasing, by the dynamic opacity optic, the intensity of the secondary adjusted light relative to an intensity of the primary adjusted light at a wavelength of the input light at which the sample in absence of the analyte absorbs greater than or equal to 80% of the primary adjusted light.

* * * * *